United States Patent
Ranne

(10) Patent No.: US 11,819,425 B2
(45) Date of Patent: Nov. 21, 2023

(54) CORACOID GUIDING SYSTEM AND A METHOD FOR USING THEREOF

(71) Applicant: CC-Instruments Oy, Turku (FI)

(72) Inventor: Juha Ranne, Turku (FI)

(73) Assignee: CC-Instruments Oy, Turku (FI)

( * ) Notice: Subject to any disclaimer, the term of this patent is extended or adjusted under 35 U.S.C. 154(b) by 356 days.

(21) Appl. No.: 17/244,146

(22) Filed: Apr. 29, 2021

(65) Prior Publication Data
US 2022/0346974 A1    Nov. 3, 2022

(51) Int. Cl.
*A61F 2/46* (2006.01)
*A61F 2/40* (2006.01)
*A61F 2/30* (2006.01)

(52) U.S. Cl.
CPC .......... *A61F 2/4612* (2013.01); *A61F 2/4081* (2013.01); *A61F 2/4657* (2013.01); *A61F 2002/30433* (2013.01); *A61F 2002/4096* (2013.01)

(58) Field of Classification Search
CPC .... A61F 2/4612; A61F 2/4081; A61F 2/4657; A61F 2002/4096; A61B 90/06; A61B 2090/062; A61B 5/1072; A61B 17/17; A61B 17/1778
See application file for complete search history.

(56) References Cited

U.S. PATENT DOCUMENTS

| | | | |
|---|---|---|---|
| 5,584,839 A * | 12/1996 | Gieringer | A61B 17/1778 606/103 |
| 5,681,333 A * | 10/1997 | Burkhart | A61B 17/1778 606/104 |
| 8,277,458 B2 * | 10/2012 | Schneider | A61B 17/0469 606/86 R |
| 8,282,643 B2 * | 10/2012 | Dross | A61B 17/1684 606/86 R |
| 9,044,222 B2 * | 6/2015 | Dross | A61B 17/0483 |
| 9,345,496 B2 * | 5/2016 | Schacherer | A61B 17/7233 |
| 10,238,378 B2 * | 3/2019 | Bonutti | A61B 17/1671 |
| 11,172,943 B2 * | 11/2021 | Arciero | A61B 17/1796 |

(Continued)

FOREIGN PATENT DOCUMENTS

| | | |
|---|---|---|
| WO | 2012170425 A1 | 12/2012 |
| WO | 2019099451 A2 | 5/2019 |

OTHER PUBLICATIONS

European Patent Office, Extended European Search Report, Application No. 22164326.5, dated Sep. 21, 2022, 7 pages.

*Primary Examiner* — Anu Ramana
(74) *Attorney, Agent, or Firm* — ZIEGLER IP LAW GROUP LLC

(57) ABSTRACT

A coracoid guiding system. The coracoid guiding system includes a coracoid grasper for holding an exteriorized coracoid bone block, and a coracoid passer. The coracoid passer has a pair of external barrels, a pair of internal barrel pins, a hollow guiding tube including an inner surface and an outer surface, and a hook gauge. The hook gauge is configured to be retractably arranged inside the hollow guiding tube. The hook gauge has a proximal end, a distal end, a curved section between the proximal end and the distal end, a first straight section extending from the proximal end to the curved section, a second straight section extending from the curved section to the distal end, wherein the distal end of the hook gauge is shaped as a hook.

19 Claims, 11 Drawing Sheets

(56) References Cited

U.S. PATENT DOCUMENTS

| | | | |
|---|---|---|---|
| 2012/0123417 A1* | 5/2012 | Smith | A61B 17/1714 |
| | | | 606/98 |
| 2012/0253352 A1 | 10/2012 | Smith | |
| 2019/0142411 A1* | 5/2019 | Bonutti | A61B 17/683 |
| | | | 606/279 |
| 2019/0321025 A1* | 10/2019 | Boileau | A61B 17/88 |
| 2021/0015503 A1* | 1/2021 | Arciero | A61B 17/1778 |

* cited by examiner

CORACOID GUIDING SYSTEM AND A METHOD FOR USING THEREOF

TECHNICAL FIELD

The present disclosure relates generally to arthroscopic procedure for fixing a gleno-humeral joint dislocation; and more specifically, to a coracoid guiding system and a method for using the coracoid guiding system for invasively attaching and/or transplanting a coracoid bone block onto anterior of a surface of a glenoid to stabilize the dislocated humerus, while locating the dislocated shoulder joint.

BACKGROUND

Human anatomy describes that the ball and socket joint allows the maximum movement than any other joints in the body. In an instance, the shoulder joint is a ball and socket joint, similar to the hip; providing allowance of three degrees of freedom i.e. pitch, yaw, and roll. Furthermore, the three degrees of freedom includes flexion-extension (motion in the sagittal plane), abduction-adduction (motion in the coronal plane), and medial-lateral rotation (motion in the transversal plane). However, the socket of the shoulder joint is extremely shallow, and apparently the most unstable joint in the human body. Moreover, the muscles and tendons serve to keep the bones in a stable position from birth, unless the shoulder experiences a sudden shock or trauma.

In order to compensate the shallow socket, the shoulder joint has a cuff of fibrous cartilage (a ligament) called a labrum that forms a cup for the head of the arm bone (humerus) to move within. Furthermore, this cuff of cartilage makes the shoulder joint much more stable, yet allows for a very wide range of movement. However, when the labrum of the shoulder joint is damaged, the stability of the shoulder joint is compromised, leading to subluxation and dislocation of the shoulder joint. Especially, successive dislocations or periodical stress to an unhealed subluxation and dislocation may cause damage to the bones of the joint i.e. the humeral head and the glenoid. Particularly, unstable or dislocated shoulder damages the anterior-inferior part of the glenoid will cause a decrease in the area of contact with the humeral head, resulting in permanent damage or loss of recovery.

Furthermore, when bone deficiencies associated with anterior shoulder instability and/dislocation occurs, the prognostic factors for the recovery/healing of soft tissues decreases. Moreover, current standards of recovery/healing are predicated on the restoration of motion and strength and the return to full functional activities. In such a scenario, re-establishment of anterior shoulder stability requires strengthening and/or treatment of the osseous defects.

Conventionally, several advancements to the surgical procedures have been developed for management of the osseous deficiencies in association with anterior shoulder instability, involving the transplantation of the coracoid process to the anterior-inferior section of the glenoid. Typically, Latarjet procedure is used that involves the transplantation of a large section of the coracoid process. Furthermore, the Latarjet procedure the large section of the coracoid process is attached together with the conjoined tendon to reinforce the glenoid fossa and create an anterior-inferior musculo-tendinous sling. However, the conventional Latarjet procedure lacks in efficient and comfortable adjustment of coracoid process together with the conjoined tendon, as the tendon does not provide the adequate support to the coracoid process. Furthermore, due to inefficient fixing or location of the dislocated joint, the patient does not acquire the comfortable movement and/or degree of freedom, and thus experiences lesser strength at the affected arm. Moreover, the patient experiences severe pain while performing the major functions such as flexion, abduction, lateral rotations, resulting in partial disability or treated as a disabled person.

Therefore, in light of the foregoing discussion, there exists a need to overcome the aforementioned drawbacks with conventional methods of treating and/or fixing subluxation and dislocation of the joints.

SUMMARY

The present disclosure seeks to provide coracoid guiding system for locating the dislocated shoulder. The present disclosure also seeks to provide a method for using a coracoid guiding system for locating the dislocated shoulder. The present disclosure also seeks to provide a coracoid passer configured to prepare an exteriorized coracoid bone block for fixation to a surface of a glenoid. The present disclosure also seeks to provide a kit including the coracoid guiding system for locating the dislocated shoulder. An aim of the present disclosure is to provide a solution that overcomes at least partially the problems encountered in prior art.

In one aspect, an embodiment of the present disclosure provides a coracoid guiding system, the coracoid guiding system comprising
  a coracoid grasper for holding an exteriorized coracoid bone block, and
  a coracoid passer configured to prepare the exteriorized coracoid bone block for fixation to a surface of a glenoid, the coracoid passer having
    a pair of external barrels,
    a pair of internal barrel pins,
    a hollow guiding tube comprising an inner surface and an outer surface, and
    a hook gauge configured to be retractably arranged inside the hollow guiding tube, the hook gauge having a proximal end, a distal end, a curved section between the proximal end and the distal end, a first straight section extending from the proximal end to the curved section, a second straight section extending from the curved section to the distal end, wherein the distal end of the hook gauge is shaped as a hook.

In another aspect, an embodiment of the present disclosure provides a coracoid passer configured to prepare an exteriorized coracoid bone block for fixation to a surface of a glenoid, the coracoid passer having
  a pair of external barrels,
  a pair of internal barrel pins,
  a hollow guiding tube comprising an inner surface and an outer surface, and
  a hook gauge configured to be retractably arranged inside the hollow guiding tube, the hook gauge having a proximal end, a distal end, a curved section between the proximal end and the distal end, a first straight section extending from the proximal end to the curved section, a second straight section extending from the curved section to the distal end, wherein the distal end of the hook gauge is shaped as a hook.

In yet another aspect, an embodiment of the present disclosure provides a kit comprising
  a coracoid guiding system,
  a screw extractor, and
  guide pins.

In yet another aspect, an embodiment of the present disclosure provides a method for using a coracoid guiding system, the method comprising
   exposing coracoid bone,
   cauterization of the coracoid bone for exteriorization of the coracoid bone block,
   preparing the exteriorized coracoid bone block for fixation to a surface of a glenoid, and
   fixating the prepared coracoid bone block to the surface of the glenoid.

Embodiments of the present disclosure substantially eliminate or at least partially address the aforementioned problems in the prior art, and enables to locate the dislocated shoulder in an efficient and effective position to allow movement of the shoulder at three degrees of freedom, post recovery.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1A:
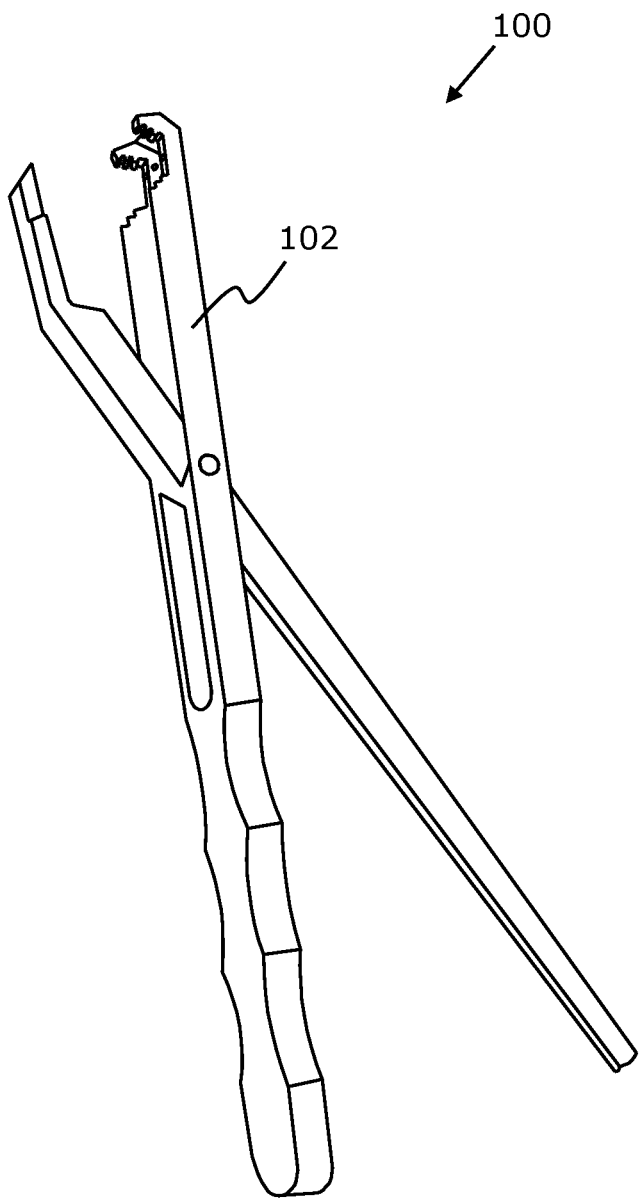
FIGS. 1A, 1B, and 1C are schematic illustrations of a coracoid guiding system, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an embodiment of the present disclosure provides a coracoid guiding system, the coracoid guiding system comprising
   a coracoid grasper for holding an exteriorized coracoid bone block, and
   a coracoid passer configured to prepare the exteriorized coracoid bone block for fixation to a surface of a glenoid, the coracoid passer having
      a pair of external barrels,
      a pair of internal barrel pins,
      a hollow guiding tube comprising an inner surface and an outer surface, and
      a hook gauge configured to be retractably arranged inside the hollow guiding tube, the hook gauge having a proximal end, a distal end, a curved section between the proximal end and the distal end, a first straight section extending from the proximal end to the curved section, a second straight section extending from the curved section to the distal end, wherein the distal end of the hook gauge is shaped as a hook.

In another aspect, an embodiment of the present disclosure provides a coracoid passer configured to prepare an exteriorized coracoid bone block for fixation to a surface of a glenoid, the coracoid passer having
   a pair of external barrels,
   a pair of internal barrel pins,
   a hollow guiding tube comprising an inner surface and an outer surface, and
   a hook gauge configured to be retractably arranged inside the hollow guiding tube, the hook gauge having a proximal end, a distal end, a curved section between the proximal end and the distal end, a first straight section extending from the proximal end to the curved section, a second straight section extending from the curved section to the distal end, wherein the distal end of the hook gauge is shaped as a hook.

In yet another aspect, an embodiment of the present disclosure provides a kit comprising
   a coracoid guiding system,
   a screw extractor,
   guide pins.

In yet another aspect, an embodiment of the present disclosure provides a method for using a coracoid guiding system, the method comprising
   exposing coracoid bone,
   cauterization of the coracoid bone for exteriorization of the coracoid bone block,
   preparing the exteriorized coracoid bone block for fixation to a surface of a glenoid, and
   fixating the prepared exteriorized coracoid bone block to the surface of the glenoid.

The present disclosure provides the aforesaid coracoid guiding system for locating a dislocated shoulder and the aforesaid method for using the coracoid guiding system. Moreover, the coracoid guiding system is implemented to prepare an exteriorized coracoid bone block that is afterwards fixed to a surface of a glenoid. Embodiments of present disclosure also provides a hook gauge configured to be retractably arranged inside a hollow guiding tube to hold the exteriorized coracoid bone block at a stable position, when the fixation of the exteriorized coracoid bone block on the surface of the glenoid is being performed. Beneficially, the hook gauge also measures a length of the exteriorized coracoid bone block. Notably, the coracoid guiding system fixes the exteriorized coracoid bone block on the surface of the glenoid in a stable position that enables the affected arm to regain the strength and movements post recovery.

Throughout the present disclosure, the term "dislocated shoulder" refers to a sudden and/or a gradual luxation or displacement of the humerus from the glenoid of the ball socket joint of the shoulder. As stated herein, the "dislocated shoulder" or "shoulder dislocation" interchangeably used in the entire document. As described in the human anatomy, the ball and socket joint of the shoulder is the most unstable joint in the human body. Furthermore, when a human being experiences sudden shock or trauma at the arms, advents the occurrence of luxation or dislocation of the humerus from the glenoid of the ball socket joint. In such a scenario, the arm loses strength and faces severe pain while performing movements of the arm.

Throughout the present disclosure, the term "coracoid guiding system" As used herein, refers to medical instruments that can be implemented to fix a dislocated shoulder, when operated. It may be appreciated that the medical instruments include medical devices, medical tools, medical apparatuses, and the like. Furthermore, the medical instruments are configured and designed to be utilised in a supervised environment that includes hospitals, laboratories, chambers, and the like, particularly performed under guidance of experts in the art. In an instance, the experts may include doctors, surgeons, and the like. In another instance, the coracoid guiding instrument may be utilized by a user that includes, but not limited to, a medical student, a medical researcher, and the like. Optionally, the coracoid guiding system As used herein, may be operated in association with a Latarjet procedure for fixation of a dislocated shoulder. As stated herein before, the Latarjet procedure is an arthroscopic operation that involves the removal and transfer of a section of the coracoid process and attached muscles to the front of the glenoid. Furthermore, the placement of the coracoid process acts as a bone block combined with transferred muscles acting as a strut, that prevents further dislocation of the joint.

Throughout the present disclosure, the term "exteriorized coracoid bone block" As used herein, refers to a piece of bone that is prepared from the coracoid process to be fixed on the surface of the glenoid. Furthermore, when the shoulder is dislocated, the humerus gets displaced from the original position i.e. the head of humerus is enclosed by the glenoid, and attached therein with a cartilage (labrum) that forms a cup for the head of the arm bone (humerus) to move within. Moreover, the exteriorized coracoid bone block is cauterized and then fixed to the surface of the glenoid. Prior to fixing, the exteriorized coracoid bone block is shaped in a cuboidal shape.

In an instance, dimensions of the exteriorised coracoid bone block vary from person to person and also depends on the amount of dislocation occurred. For example, when a person of 5 feet height and a person of 6 feet height is injured from shoulder dislocation, then the dimensions of the exteriorised coracoid bone block will be relatively smaller for the person with 5 feet height than the person of 6 feet height.

The coracoid guiding system comprises a coracoid grasper for holding an exteriorized coracoid bone block. As used herein, the term "coracoid grasper" is a medical instrument used to hold, grasp or seize a bone block therein to hold until the further process is carried therefrom. It may be appreciated the coracoid grasper is manufactured using stainless steel, cobalt-chrome alloy, titanium, nickel-titanium alloy (nitinol), and the like. In an embodiment, the coracoid grasper mimics a shape of a clipper. The coracoid grasper includes a pair of claws at the front end of and a pair of extended members at the rear end. Furthermore, the pair of claws includes a flat element and a curved element, to receive a piece of bone block therein. The pair of claws includes curved ends to firmly hold the piece of bone block when received. Optionally, the coracoid grasper may include blunt teeth at the inner sides to provide increased grip while holding the piece of bone block therein. In an example, at least one of the extended member of the pair of extended members includes wave like structure at lateral sides to provide increased grip when a user holds the coracoid grasper. In an instance, the coracoid grasper may hold the exteriorised coracoid bone block in a transverse position or a longitudinal position according to the requirement.

The coracoid guiding system comprises a coracoid passer configured to prepare the exteriorized coracoid bone block for fixation to a surface of a glenoid. As used herein, the term "coracoid passer" refers to medical instruments, when in operation, configured to fix the exteriorized coracoid bone block onto the surface of the glenoid. In an instance, the coracoid passer includes a top part and a bottom part. The top part includes a curved cuboidal plate attached to an elongated member. Structurally, the elongated member includes a flat part at the top, a curved part at the intermediate and a broader base at the bottom. The curved cuboidal plate is attached to the flat part of the elongated member. Furthermore, the curved cuboidal plate and the flat part are conjoined together to form the top part of the coracoid passer.

Moreover, the coracoid passer includes
a pair of external barrels,
a pair of internal barrel pins,
a hollow guiding tube comprising an inner surface and an outer surface, and
a hook gauge configured to be retractably arranged inside the hollow guiding tube, the hook gauge having a proximal end, a distal end, a curved section between the proximal end and the distal end, a first straight section extending from the proximal end to the curved section, a second straight section extending from the curved section to the distal end, wherein the distal end of the hook gauge is shaped as a hook.

In this regard, the pair of external barrels are arranged to the top part of the coracoid passer. The term "external barrels" As used herein, refers to hollow cylindrical tubes, when in operation, configured to receive and retract cylindrical and/or elongated instruments, such as, but not limited to, cylindrical pins, drill extensions, and the like. In an example, the pair of external barrels includes internal diameter in a range of 3 mm to 5 mm. Furthermore, a length of the pair of external barrels ranges from 60 mm to 80 mm. The length of the pair of external barrels can be for example from 60, 65, 70 or 75 mm up to 65, 70, 75 or 80 mm, and the internal diameter of the pair of external barrels can be for example from 3, 3.5, 4 or 4.5 mm up to 3.5, 4, 4.5 or 5 mm.

Moreover, the pair of internal barrel pins, when in operation, are configured to be inserted inside the pair of external barrels. As stated herein, the pair of internal barrel pins refer to hollow cylindrical conduits, tubes, and the like, configured to receive and/or retract drills, pins, and the like. It will be appreciated that the internal diameter of the pair of internal barrel pins is relatively smaller than the pair of external barrels to be received therein and/or retracted therefrom. In an example, the internal diameter of the pair of internal barrel pins in a range of 2 mm or 4 mm. In an instance, a length of the pair of internal barrel pins is relatively greater than the pair of external barrels. In another instance, the pair of internal barrel pins is passed entirely through the pair of external barrels, and thereby a part of the pair of internal barrel pins is outside the pair of external barrels at the front end. In such an instance, one-fourth part of the pair of internal barrel pins extends outside the pair of external barrels. When in use a pair of guide pins can be inserted via the internal barrels pins. The pair of guide pins is used to guiding hollow screws to appropriate place in patient body.

Moreover, the hollow guiding tube comprises an inner surface and an outer surface. As used herein, the hollow guiding tube refers to a cylindrical element placed at a downstream of the pair of external barrels. In an example, the hollow guiding tube is retractably mounted to the coracoid passer, when in operation. Furthermore, the hollow guiding tube includes an external diameter circumference extending to the outer surface and an internal diameter circumference extending to the inner surface, defining a thickness of the curved surface of the hollow guiding tube. In an instance, the thickness of the curved surface of the hollow guiding tube ranges from 0.2 mm to 0.8 mm. In another instance, an internal diameter of the hollow guiding tube ranges from 2 mm to 5 mm.

Furthermore, the hook gauge configured to be retractably arranged inside the hollow guiding tube. As used herein, the hook gauge refers to a solid cylindrical element that measures and holds the exteriorized coracoid bone block, when in operation. The hook gauge includes the proximal end, the distal end, and the curved section between the proximal end and the distal end. Furthermore, the first straight section extends from the proximal end to the curved section and the second straight section extends from the curved section to the distal end.

The distal end of the hook gauge is shaped as a hook. In an instance, the proximal end, the distal end, and the curved section are integral to each other. In an embodiment, the distal end forms the hook and includes a narrower tip at a distal end. In an example, the distal end and the curved section form a one-twentieth part of the hook gauge. In another example, a length of the hook gauge is relatively greater than the hollow guiding tube. In such an instance, when the hook gauge is completely inserted inside the hollow guiding tube, at least a one-fifth of the first straight section, the curved section and the second straight section extends outside the hollow guiding tube. Furthermore, at least a one-fifth of the first straight section, the curved section and the second straight section extends double the length of the one-fourth part of the pair of internal barrel pins extending outside of the pair of external barrels.

Optionally, the curved section of the hook gauge, and at least a part of the second straight section and/or the first straight section is arranged inside the hollow guiding tube, when in use. The hollow guiding tube allows an insertion of the curved section of the hook gauge, and at a part of the second straight section at the mouth of the hollow guiding tube. Subsequently, when the hook gauge is inserted inside the hollow guiding tube, the first straight section is received inside the hollow guiding tube. In an instance, when the hook gauge is passed through the hollow guiding tube; the distal end, the curved section, and the at least a part of the second straight section is outside the hollow guiding tube at the front end of the hollow guiding tube. Alternatively, the diameter of the guiding tube is same as the diameter of the hook gauge. In an embodiment, the internal diameter of the hook gauge provides a fit tolerance for insertion of the hook gauge.

Optionally, the curved section creates a frictional force between the inner surface of the hollow guiding tube and at least a part of the hook gauge inside of the hollow guiding tube. Furthermore, the inner surface of the hollow guiding tube is close fit to the curved section, and thereby provides a tight fit insertion of the hook gauge inside the hollow guiding tube. In an instance, the curved section and the suspended tip of the second straight section of the hook gauge, slides in contact with the inner curved surface of the hollow guiding tube, while passing the hook gauge inside the hollow guiding tube. In such an instance, a sliding friction force between the inner surface of the hollow guiding tube and at least a part of the hook gauge inside of the hollow guiding tube. Beneficially, the internal sliding friction force between the hook gauge and hollow guiding tube enables a smooth transition of the hook gauge when passed through the hollow guiding tube. In one example the total length of the hook gauge is 170 mm and length of the curved section is between 40-100 mm. The radius r of a curvature of the curved section can be for example from 200, 300, 400, 500, 600, 700, 800, 900, 1000, 2000, 4000, 8000, 10000, mm to 500, 600, 700, 800, 900, 1000, 2000, 4000, 8000, 10000, 13000 mm. Indeed the curvature is selected to have smaller value if desired sliding friction is higher and it is selected to have higher value if the desired sliding friction is lower. This way the sliding friction can be controlled. Furthermore selection of material for the hook gauge has impact on resulting friction. If material is very flexible then the curvature is selected to have smaller value (shorter r) and if it is more rigid then the curvature is selected to have larger value (longer r). In general the radius r can be calculated $r=(h^2+d^2/4)/2h$ where in d is length of the curved section and h "amount of bending" of the curved section. Amount of bending refers to distance h between a planar surface and highest gap value, between the curved section when the hook gauge is set in the planar surface. In one embodiment the radius is between 2000 to 6000 mm and material stainless steel to obtain a preferable friction.

Optionally, the exteriorised coracoid bone block has a length of 20-25 mm, width of 10-14 mm and a thickness of 10-14 mm. The thickness of the coracoid bone block can be for example from 10, 11, 12 or 13 mm up to 11, 12, 13 or 14 mm. In an instance, the dimensions are based on a body structure of the patient and the amount of injury caused due to dislocation of humerus from the glenoid. As stated herein above, the exteriorised coracoid bone block is prepared in a cuboidal shape or in a tubular structure to act as a strut to hold the humerus in a static position, when the dislocated shoulder is relocated.

Optionally, the hook gauge is comprises scale points to measure cross section of at least one of the glenoid and the coracoid. Furthermore, the proximal end of the hook gauge is provided with scale points to measure the displacement of the hook gauge inside the hollow guiding tube, that provides a measurement of the at least one of the glenoid and the coracoid. The measurement scale provided on the hook gauge is configured with inscribed slits equidistantly. Operationally, when the hook gauge slides through the hollow guiding tube, the displacement from an initial slit to an intermediate slit or to a final slit, defines the measurement. In an instance, the second straight end of the hook gauge extends to a length of the glenoid and/or the coracoid. In such an instance, a visual displacement of the inscribed slides defines the measurement of the at least one of the glenoid and the coracoid. As stated herein above, the thickness of the exteriorised coracoid bone block ranges from 10 mm to 14 mm, and the length of the glenoid ranges from 30 mm to 40 mm. The length of the glenoid can be for example from 30, 32, 34, 36 or 38 mm up to 32, 34, 36, 38 or 40 mm.

Optionally, the hook gauge is operable to hold the exteriorised coracoid bone block and the glenoid together. The hook of the hook gauge traverses through a combined length of the glenoid and the coracoid bone block, and the hook clamps at a distal end surface of the glenoid. In such an instance, the distal end surface may include soft tissue, may be pressed when the hook and the distal end of the pair drill pins are clamped together to hold the exteriorised coracoid bone block and the glenoid together. Alternatively, the hook is in proximity with the glenoid and the second part traverses along the combined lengths of the glenoid and the exteriorised coracoid bone block. Particularly, when combined lengths of the glenoid and the exteriorised coracoid bone block is located then the hook and the distal end of the pair drill pins holds in combination. For example, the combined length of the glenoid and the exteriorised coracoid bone block ranges from 30 mm to 54 mm. The combined length of the glenoid and the exteriorised coracoid bone block can be for example from 30, 32, 34, 36, 38, 40, 42, 44, 46, 48, 50 or 52 mm up to 34, 36, 38, 40, 42, 44, 46, 48, 50, 52 or 54 mm.

Optionally, the coracoid guiding system comprises a pair of guide pins to guide hollow screws for fastening the exteriorised coracoid bone block to the surface of the glenoid. As used herein, the term "hollow screw" refers to fasteners or bolts used to be drilled inside the body to secure or restrict a movement between the attached surfaces. Furthermore, the hollow screws are manufactured using titanium and are biodegradable. Alternatively, optionally, the hollow screws are made of an inert metal and or an alloy thereof, such as stainless steel for example. Moreover, the hollow screws are drilled inside the bones to establish a secure attachment there between. The hollow screws are drilled inside the exteriorised coracoid bone block and the glenoid to securely locate and fix the exteriorised coracoid bone block to the surface of the glenoid. The pair of guide pins is dimensioned to fit thru the hollow screws. The pair of guide pins are inserted to appropriate target in human body via the pair internal barrel pins when in use. The outer diameter of the guide pins is less than inner diameter of internal barrel pins. The guide pins are inserted via the internal barrel pints to bone. After that the coranoid passer is removed and hollow screws are guided via the guide pins to the bone. The hollow screws have opening from proximal and to distal end of the screw. The opening is dimensioned in a way that the guiding pins can go thru the screw.

Optionally, length of screws is lesser that the combined lengths of the glenoid and the exteriorised coracoid bone block. As mentioned herein above, the combined length of the glenoid and the coracoid bone block includes summation of the ranges of length of the glenoid and the exteriorised coracoid bone block. For example, the length of screws ranges from 30 mm to 36 mm. The combined length of the glenoid and the exteriorised coracoid bone block can be for example from 30, 31 32, 33, 34 or 35 mm up to 31, 32, 33, 34, 35 or 36 mm.

Optionally, the coracoid guiding system includes a screw extractor for withdrawing the hollow screws from the glenoid-coracoid bone block. a screw extractor configured to extract the screws, when in operation. As used herein, the term "screw extractor" refers to a screw guiding element, that enables an extraction of the screws, when in operation. Furthermore, the screw extractor includes a male mating element at a distal end and a thick head a proximal end to hold the screw extractor. Moreover, when in operation, the male mating part couples to a female part (screw head) of the screw, to retract, when rotated anticlockwise direction. In an embodiment, the screw extractor is inserted along one of the guide pins to locate the hollow screw and to retracted the hollow screw therefrom. In an example, the screw extractor includes a solid cylindrical body, including a length double to the length of the pair of internal barrel pins.

The present disclosure also relates to the coracoid passer as described above. Various embodiments and variants disclosed above apply mutatis mutandis to the coracoid passer.

The coracoid passer configured to prepare an exteriorized coracoid bone block for fixation to a surface of a glenoid, the coracoid passer having
   a pair of external barrels,
   a pair of internal barrel pins,
   a hollow guiding tube comprising an inner surface and an outer surface, and
   a hook gauge configured to be retractably arranged inside the hollow guiding tube, the hook gauge having a proximal end, a distal end, a curved section between the proximal end and the distal end, a first straight section extending from the proximal end to the curved section, a second straight section extending from the curved section to the distal end, wherein the distal end of the hook gauge is shaped as a hook.

Optionally, the coracoid passer further comprises screws for fastening the exteriorised coracoid bone block to the surface of the glenoid.

The present disclosure also relates to the kit as described above. Various embodiments and variants disclosed above apply mutatis mutandis to the kit.

Furthermore, a kit is provided to operate the dislocated shoulder. As used herein, the term "kit" refers to a cuboidal box, a cuboidal case, or a container containing the medical instruments. Furthermore, the medical instruments may include, but not limited to, scissors, retractors, clamps, bone saws, files, drills, and the like, that are used as medical equipment. For example, the kit may include, but not limited to, a medical kit, medical tool kit, an operational kit, and the like. Notably, the kit may be considered as an assembly of medical instruments or tools that are used to perform the procedure or the operation.

The kit comprises the aforesaid coracoid guiding system for locating the dislocated shoulder. Furthermore, the kit includes the coracoid guiding system as one of the essential equipment to perform the operation (locating the dislocated shoulder). Moreover, the coracoid guiding system, as included in the kit, configured to perform the major part of operation by efficiently locating the exteriorised coracoid bone block to the surface of the bone block. It may be appreciated that the coracoid guiding system performs in association with other medical equipment (such as, but not limited to, scissors, retractors, clamps, bone saws, files, drills, and the like) that are present in the kit and used for performing the operation (locating the dislocated shoulder).

Kit comprises a screw extractor. As used herein, the term "screw extractor" refers to a screw guiding element or a screw extracting pin, that enables an extraction of the screws from the bone. Furthermore, the screw extractor includes a male mating element at a distal end and a thick head a proximal end to hold the screw extractor. In a scenario, if the intruded screws cause irritation or may be there occurs a requirement to replace or remove the screws, then the screw extractor is used to retract the screws.

Furthermore the kit comprises guide pins. The guide pins refer to pins which are dimensioned to be suitable to be inserted via the pair of internal barrel pins to bone. The guide pins are used to guide hollow screws to holes in the bone to enable screwing the screws to the bone.

Kit might comprise arthroscope. As used herein, the term "arthroscope" refers to a medical instrument or medical equipment, configured to inspect or operate an anterior or interior of a joint in a human body. Typically, arthroscope includes a narrower tip at a distal end and a viewing device or an imaging device at a proximal end. The viewing device or the imaging device is configured to view inside the human body i.e. soft tissues and in between the joints. Specifically, the arthroscope is inserted and moved to a lateral portal position of the shoulder joint using a switching stick. Moreover, the switching sticks acts as a guiding element to locate the arthroscope within the joints to access a neck of the coracoid process and the glenoid. In such an instance, the access to the neck of the coracoid process and the glenoid allows a wide view of the dimensions of the coracoid process and the glenoid for better visualisation.

Kit might comprise an oscillating saw. As used herein, the term "oscillating saw" refers to a "medical equipment" or an "operation saw" that is electric driven. The oscillating saw is configured to precisely cut bones and hard tissues without harming the soft tissues or veins in a proximity thereto. Furthermore, the oscillating saw functions by moving an attachment at high-speed in a rotating or back-and-forth motion that allows for precise control with minimal vibration. The attachment includes saw blades, grinding discs, and the like. Typically, the attachment of the oscillating saw is inserted to a depth of a site to cut and then the rotating or back-and-forth motion enable a cutting of a facet of the exteriorised bone block.

Kit might comprise cautery. As used herein, the term "cautery" refers to a medical instrument or a medical tool, configured to cauterize soft tissues in précised dimension. Typically, cautery also known as "electrocautery" or "thermocautery", functions when a direct or alternating current is passed through a resistant metal wire electrode for generating heat. Furthermore, the heated electrode is then applied to living tissue to achieve hemostasis or varying degrees of tissue destruction or for cauterisation of bones. Moreover, the cautery is used to precisely cut the coracoid bone block of the coracoid process in a précised dimension as desired, while ensure no harm to the soft tissues and veins in the proximity thereto.

Kit might comprise scalpel. As used herein, the term "scalpel" refers to sharp medical tools or medical instruments for performing anatomical, incision, dissection, podiatry and the like. The scalpel is used for performing incision in the skin and/or muscle at a defined part of a human body, to insert medical instruments and/or tools therein for further operation. In an instance, the scalpel is implemented to incise opening in a proximity of the ball and socket joint around the shoulder. In an example, one or scalpels may be used according to the dimension of incision to be performed.

Kit might comprise fibre sticks. As used herein, the term "fibre sticks" refers to intraoperative suture tensioning prior to committing an anchor in bone, allowing for precise tissue reduction. Furthermore, the fibre is manufactured using poly fibre materials to avoid infection when utilised for suture of a stitch or row of stitches holding together edges of a wound or a surgical incision. In an instance, when the exteriorized bone block is located on the surface of glenoid, then suture is performed on the incision using the fibre sticks. In another example, the suture may be provided temporarily or permanently based on the requirement post operation.

Kit might comprise fibre tap. As used herein, the term "fibre tape" refers to suture tapes.

Kit might comprise non-stretch rigid tape. As used herein, the term "non-stretch rigid tape" refers to a highly dense poly fabric tape used for providing secured sealing to a wound or surgical incision. Typically, non-stretchable rigid tape is implemented as a tiger tape, and is used for firmly attaching the edges of the skin in the proximity of the wound or the surgical incision. In an instance, the fibre tapes and tiger tapes are used layer by layer on the site of the wound or the surgical incision to ensure a sealing and thereby no further leakage of blood tissue therefrom.

Optionally, the kit comprises hollow screws for fastening the exteriorised coracoid bone block to the surface of the glenoid. Typically hollow screws are provided separately as the hollow screws will remain in the body after the operation.

It will be appreciated that the procedure or operation procedure or Latarjet procedure for locating the dislocated shoulder is performed in a supervised environment under guidance of experts such as doctors, surgeons and the like. Prior to initiation of the initiating the operation procedure or Latarjet procedure, basic tests such as anterior apprehension test, jobe relocation test, and the like, are carried out to ensure a dislocation of the shoulder of a patient. At initiation of procedure, the patient is placed in the beach chair position and affected arm is kept in holder and ensured about freedom of rotation of the arm. Typically, the procedure is carried out with a five portal technique. The required portals are posterior (P), lateral (L), anterolateral (AL), antero-superior (AS), and antero-inferior (AI). Subsequently, an arthroscope is inserted transversely through the posterior portal. The arthroscope is inserted and moved to a lateral portal position of the shoulder joint using a switching stick, to inspect an interior position of the glenoid and the coracoid process.

The present disclosure also relates to the method as described above. Various embodiments and variants disclosed above apply mutatis mutandis to the method.

The method for using a coracoid guiding system comprises exposing coracoid bone. As used herein, above, the coracoid guiding system is used together with other medical instruments or tools, such as for example provided in the aforesaid kit, or used by medical professionals, to operate the location of the dislocated shoulder. While initiating exposure of the coracoid bone, the lateral portal is marked with a needle in front of the biceps and tendon, allowing access to the anterior glenoid, the subscapularis tendon, and the coracoid process. Subsequently, a skin incision is made with the scalpel to create an opening that is completed using scissors on the anterior edge of the subscapularis tendon. The skin incision is wide enough to allow an exteriorisation of the coracoid process. In an example, the incision may be made up to 25 mm to allow the exteriorisation of the coracoid process without any friction at the wound edges. In subsequent to incision, splitting of the subscapularis tendon is performed through the anterinferior and anterolateral portals as viewed from the lateral and enterolateral portals. Furthermore, according to alternative example to elbow arthroscopy, the surgery can be performed as an open surgery.

The method comprises cauterization of the coracoid bone for exteriorization of the coracoid bone block. The cauterization of the coracoid bone is typically performed using the cautery. Moreover, the cautery is an electrocautery and electric driven. In an instance, opening of the subscapularis tendon is conducted using scissors or the electrocautery. Subsequently, a tiger tape is placed through the split to elevate a superior part of the subscapularis tendon accomplish the completion of the split. In such a scenario, allowance of split is carefully established so as to exteriorise the coracoid bone block. Moreover, establishment of exteriorization of the coracoid bone block is performed while ensure no harm to the nerves or veins in the proximity. As soon as the coracoid bone block is exteriorised, the grasper is used to hold the exteriorised bone block in an upraised position above the wound.

The method comprises preparing the exteriorized coracoid bone block for fixation to a surface of a glenoid. As stated above, the grasper is used to pull out the exteriorised coracoid bone block. In furtherance to that, the exteriorized coracoid bone block is prepared for fixation to a surface of the glenoid, when held in an upright position. Furthermore, the exteriorized coracoid bone block is transversely held using the grasper at anterolateral portal. Moreover, preparation includes producing the exteriorized coracoid bone block in accordance with glenoid to fix therein and locate the humerus fossa.

Optionally, preparing the exteriorized coracoid bone block comprises shaping of the exteriorized coracoid bone block. The exteriorized coracoid bone block held in an upright position when an oscillating saw is implemented to produce a cuboidal shape of the exteriorized coracoid bone block, while extruding the soft tissues attached thereto. Furthermore, the oscillating saw is operated back and forth to yield the cuboidal shape in précised dimension as discussed herein above. Moreover, shaping includes removing the undesired protrusions, or hard tissues attached to the exteriorized coracoid bone block.

Optionally, preparing the exteriorized coracoid bone block comprises positioning drill holes in the coracoid bone block. Furthermore, the shaped exteriorized coracoid bone block is clamped within the hook of the hook gauge and the distal ends of the pair of internal barrel pins. Moreover, the drill holes are longitudinally and transversely positioned across the depth of the exteriorized coracoid bone block. As stated herein above, the pair of internal barrel pins are passed through the cross section of the exteriorized coracoid bone block.

Optionally, preparing the exteriorized coracoid bone block comprises placing the coracoid bone block parallel to a surface of the glenoid. Furthermore, the drilled exteriorized coracoid bone block is positioned to a surface of the glenoid, while holding the coracoid passer perpendicular to the exteriorized coracoid bone block. In such an instance, the distal side of the coracoid bone block is placed parallel to the front surface of the glenoid so as to hold the humerus in a located position. Moreover, the coracoid bone block is placed at a distance of 1-2 mm from the surface of the glenoid.

The method comprises fixating the prepared coracoid bone block to the surface of the glenoid. The pair of internal barrel pins are passed through a depth lesser of the cross section of the coracoid bone block. As for example, the combined length of the coracoid bone block and the glenoid is 44 mm, then the screws are drilled to a depth of 36 mm therein to fix the coracoid bone block to the surface of the glenoid. The hollow screws are retractably inserted through a self-drilling screw via a guiding pin. Optionally, the hollow screws may be retracted using the screw extractor whenever required.

Optionally, the exteriorized coracoid bone block being placed parallel to the surface of the glenoid uses a frictional force between the inner surface of the hollow guiding tube and at least a part of the hook gauge inside of the hollow guiding tube.

DETAILED DESCRIPTION OF THE DRAWINGS

Figure 1B:
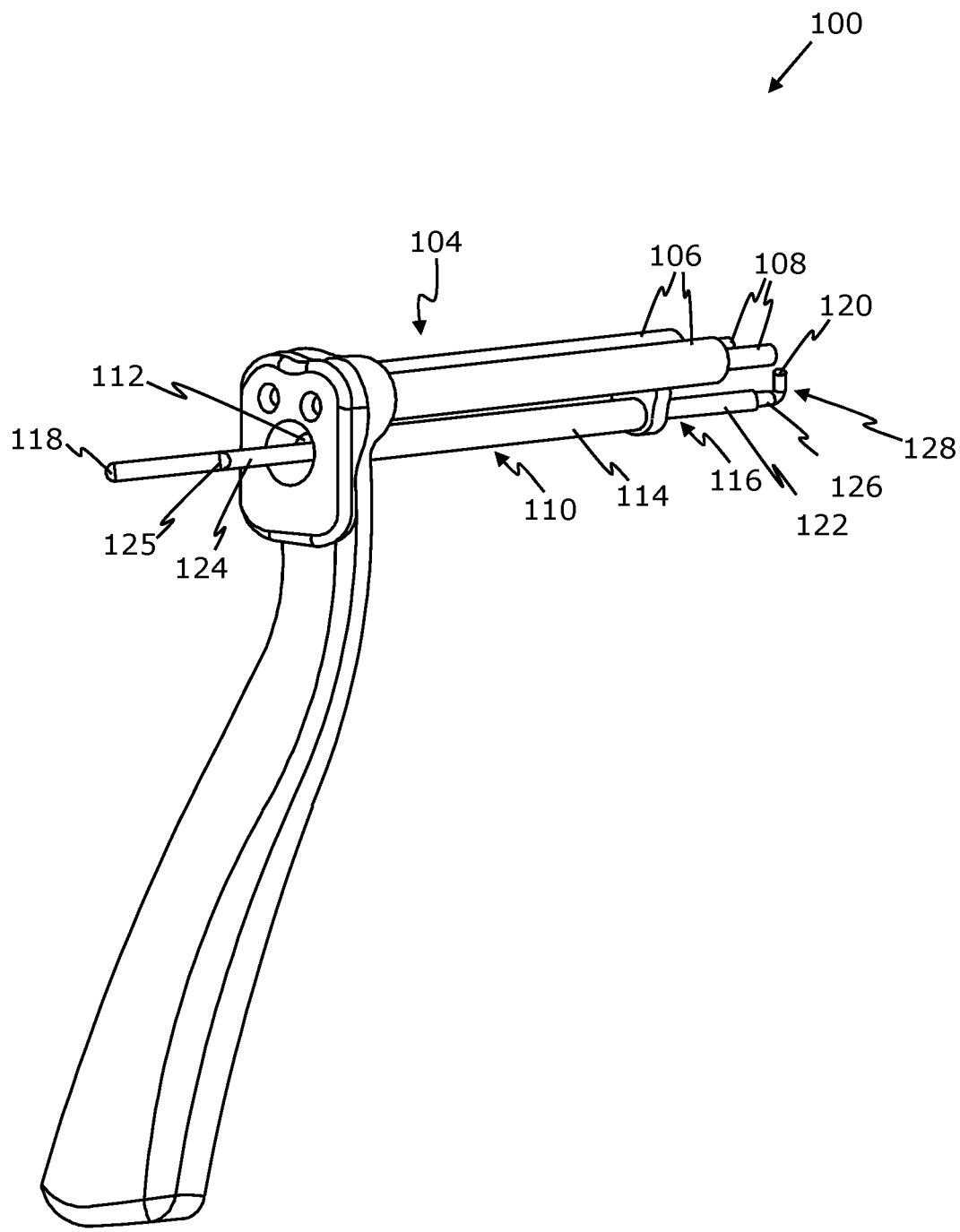
Figure 1C:
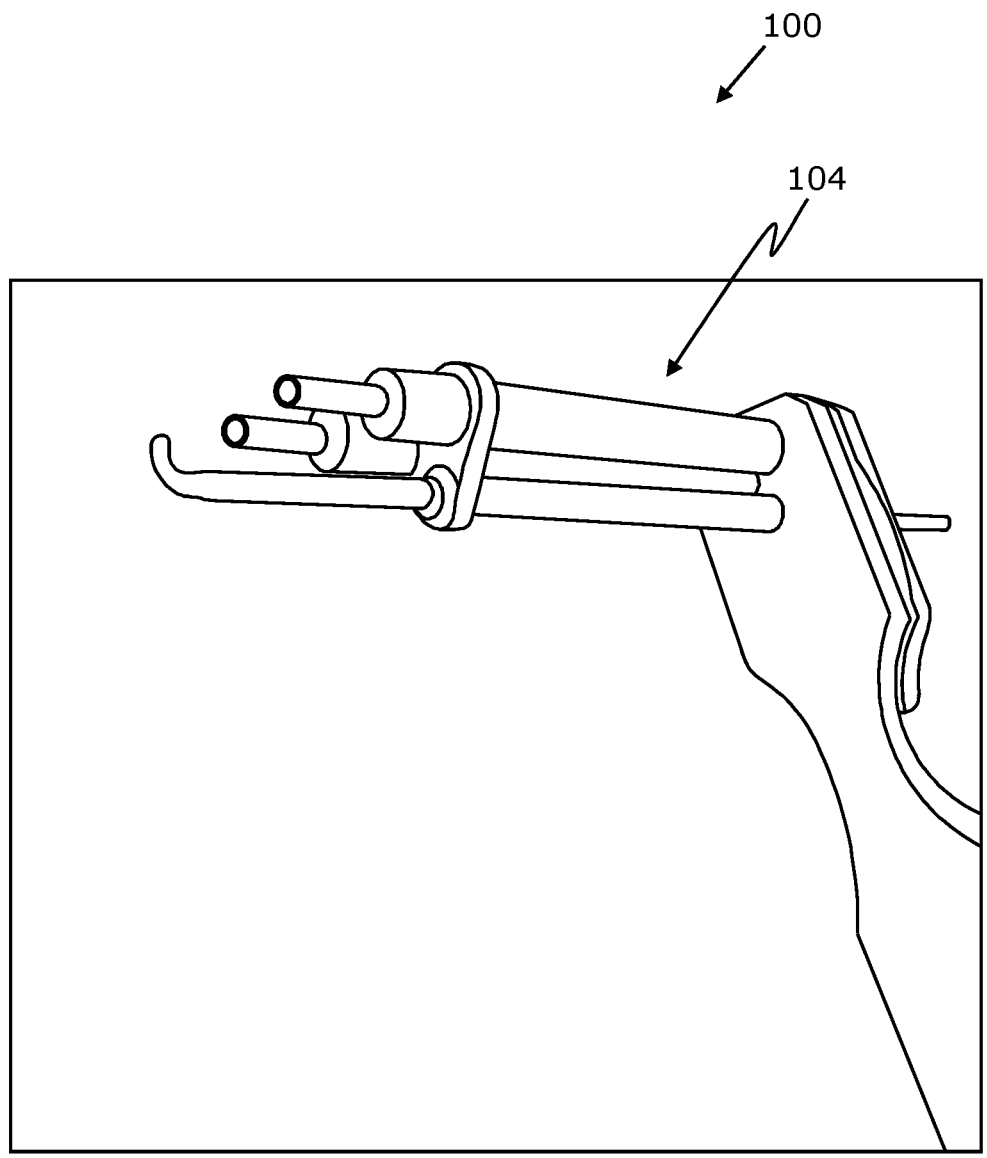

Referring to FIGS. 1A, 1B, and 1C, illustrated is a schematic illustration of a coracoid guiding system 100, in accordance with an embodiment of the present disclosure. The coracoid guiding system comprises a coracoid grasper 102 for holding an exteriorized coracoid bone block, a coracoid passer 104 configured to prepare the exteriorized coracoid bone block for fixation to a surface of a glenoid, the coracoid passer having a pair of external barrels 106, a pair of internal barrel pins 108, a hollow guiding tube 110 comprising an inner surface 112 and an outer surface 114, a hook gauge 116 configured to be retractably arranged inside the hollow guiding tube 110, the hook gauge having a proximal end 118, a distal end 120, a curved section 122 between the proximal end and the distal end, a first straight section 124 extending from the proximal end to the curved section, a second straight section 126 extending from the curved section to the distal end, wherein the distal end of the hook gauge is shaped as a hook 128. The hook gauge 116 further comprises a scale points 125 i.e. measurement markings. The scale points 125 indicate to the user distance between the hook 128 of the hook gauge 116 and distal end of the of hollow guiding tube 114. This indication can be used to measure cross section of at least one of: the glenoid and the coracoid. This is useful as the user can use the indication for example to select appropriate length for screws to be used during use of the system.

Figure 2:
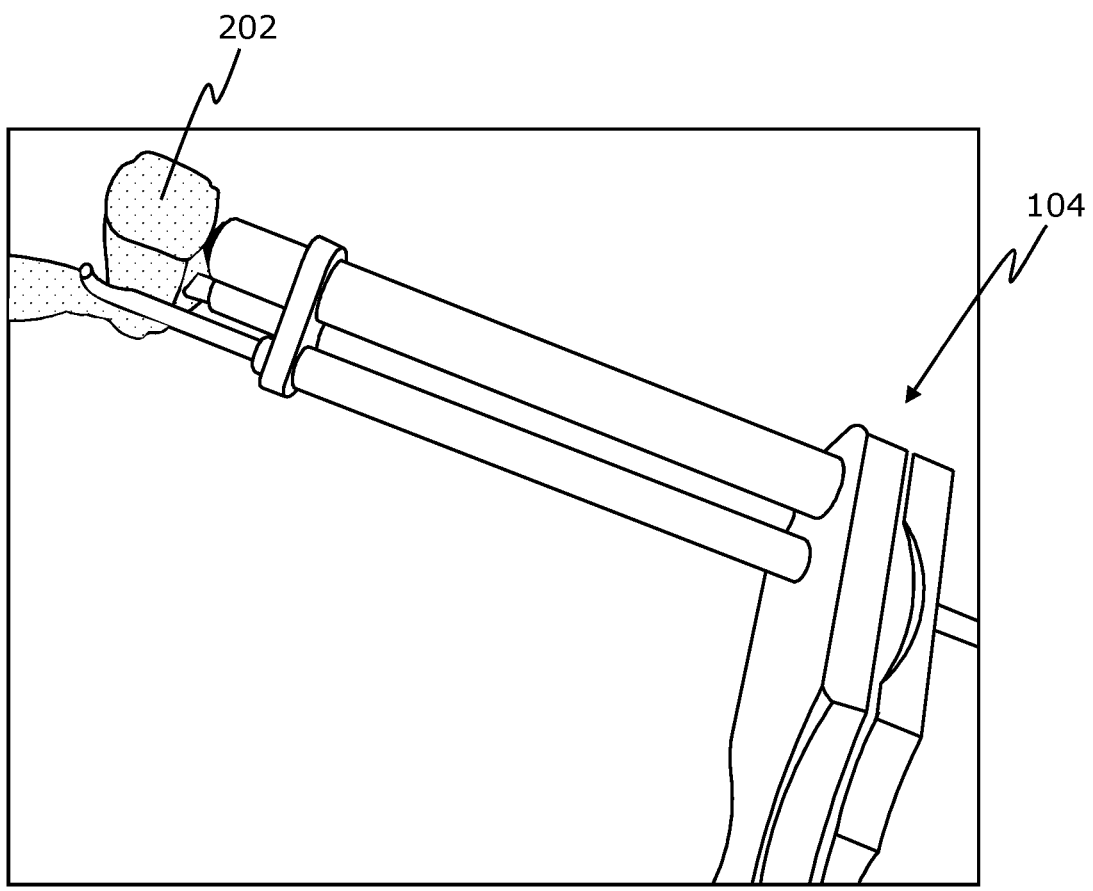
FIG. 2 is a schematic illustration of the coracoid grasper holding an exteriorized coracoid bone block, in accordance with an embodiment of the present disclosure.

Referring to FIG. 2, illustrated is a schematic illustration of the coracoid grasper 104 holding an exteriorized coracoid bone block 202, in accordance with an embodiment of the present disclosure.

Figure 3A:
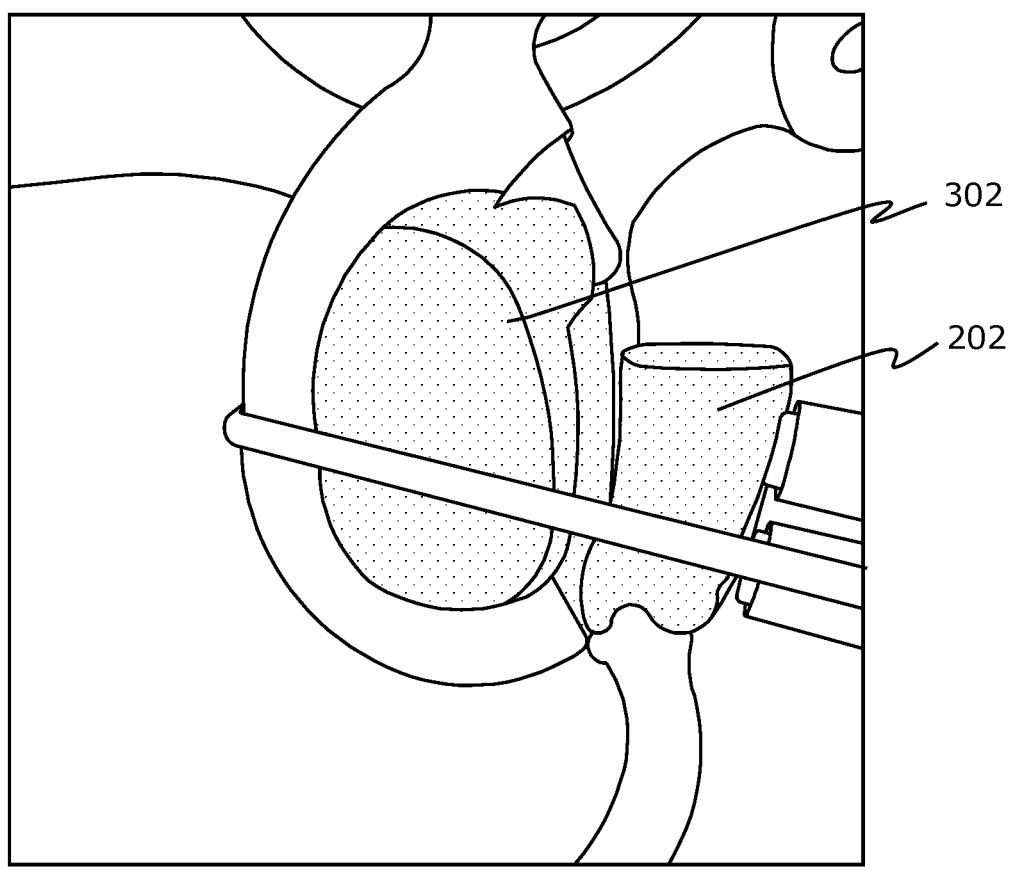
FIGS. 3A and 3B are schematic illustrations of the coracoid grasper holding an exteriorized coracoid bone block and the glenoid, in accordance with an embodiment of the present disclosure.
Figure 3B:
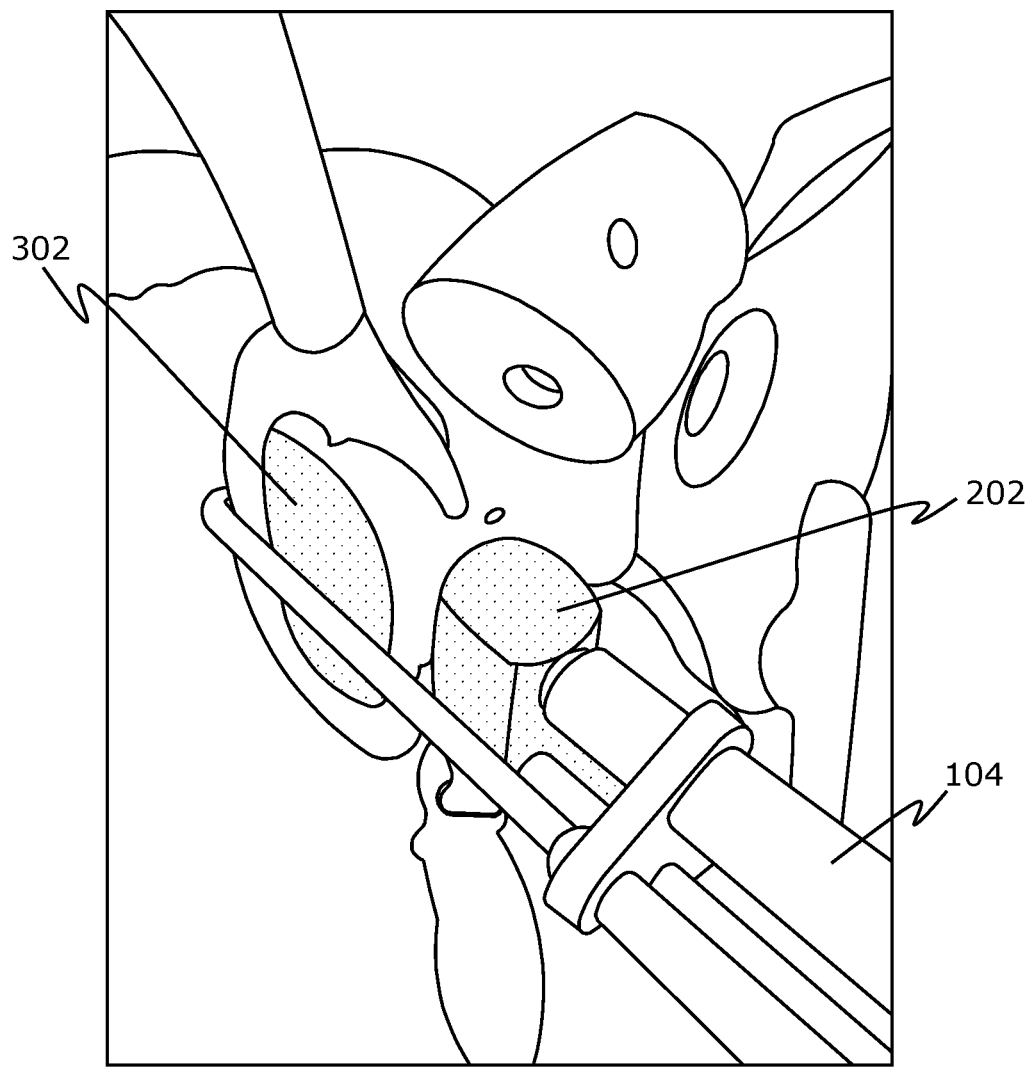

Referring to FIGS. 3A, and 3B illustrated are schematic illustrations of the coracoid grasper 104 holding an exteriorized coracoid bone block 202 and the glenoid 302, in accordance with an embodiment of the present disclosure.

Figure 4:
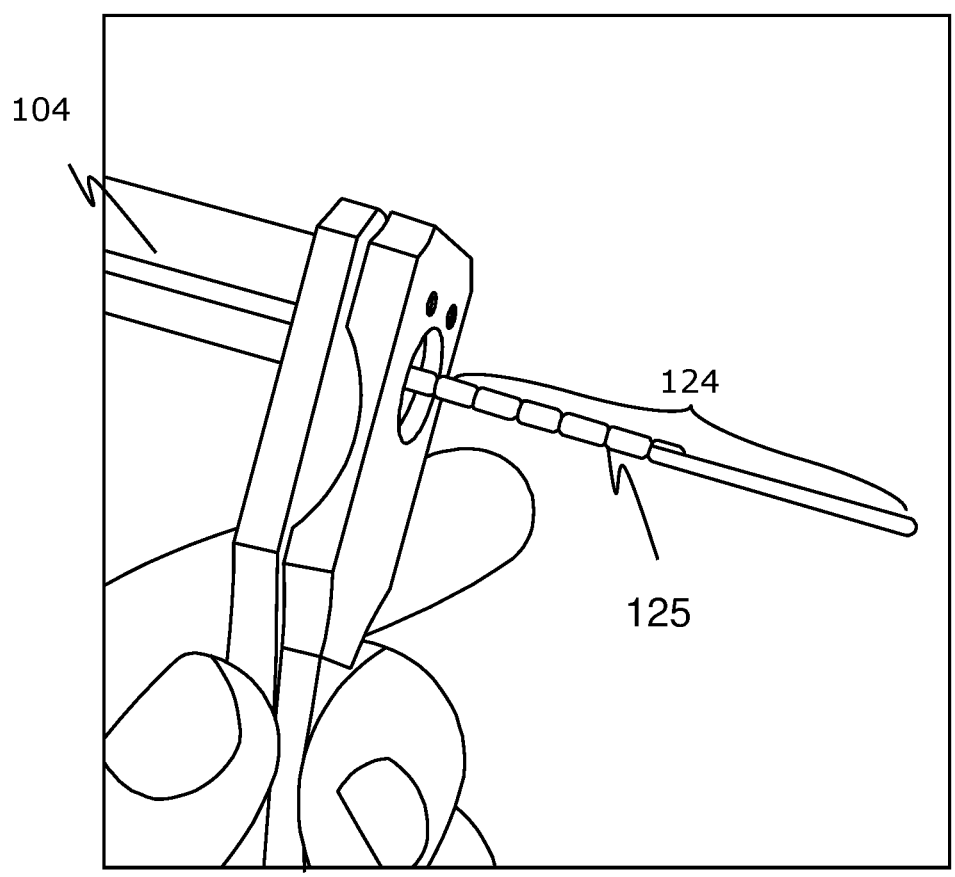
FIG. 4 is a schematic illustration of the coracoid grasper along with the first straight end, in accordance with an embodiment of the present disclosure.

Referring to FIG. 4, illustrated is a schematic illustration of the coracoid grasper 104 along with the first straight end 124 and the scale points 126 in accordance with an embodiment of the present disclosure.

Figure 5:
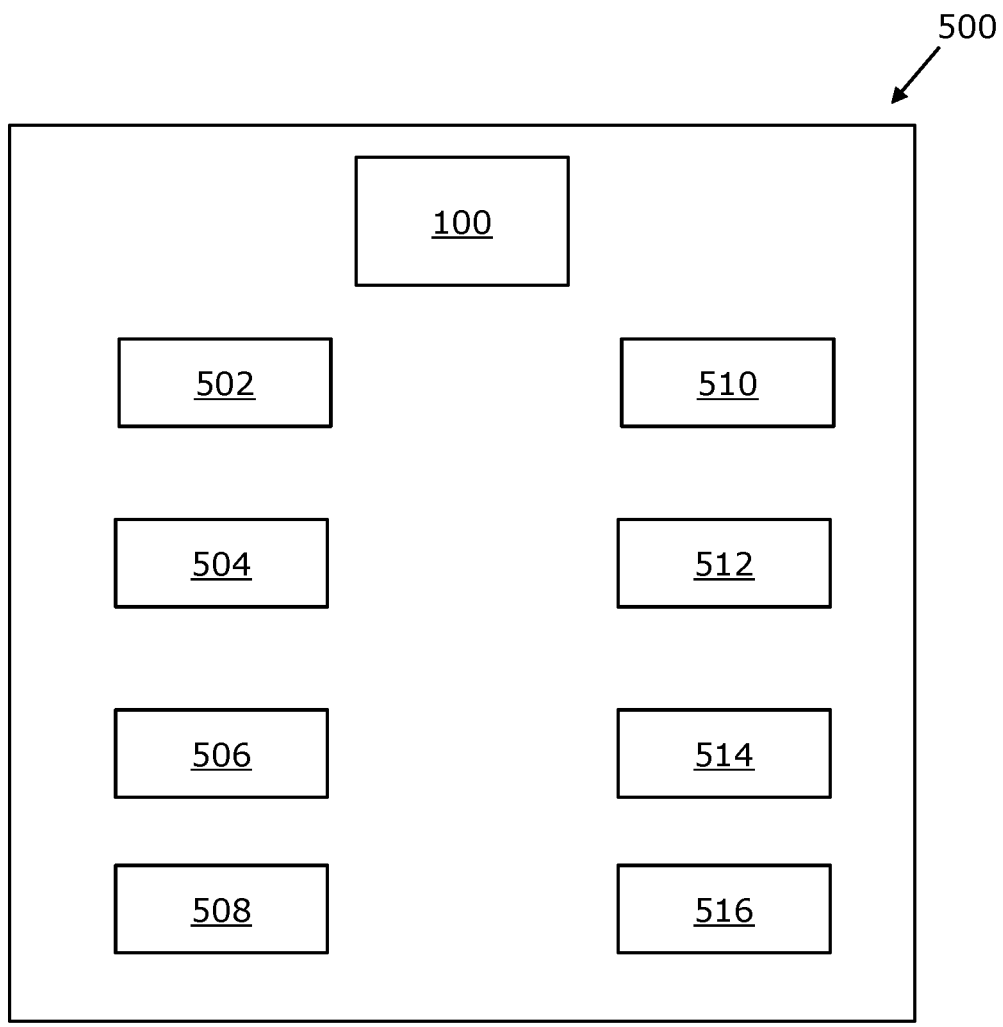
FIG. 5 is a schematic illustration of a kit, in accordance with an embodiment of the present disclosure.

Referring to FIG. 5, illustrated is a schematic illustration of a kit 500, in accordance with an embodiment of the present disclosure. The kit 500 comprises the coracoid guiding system 100, a screw extractor 502, an arthroscope 504, an oscillating saw 506, a cautery 508, a scalpel 510, fibre sticks 512, a fibre tape 514, and a non-stretch rigid tape 516.

Figure 6:
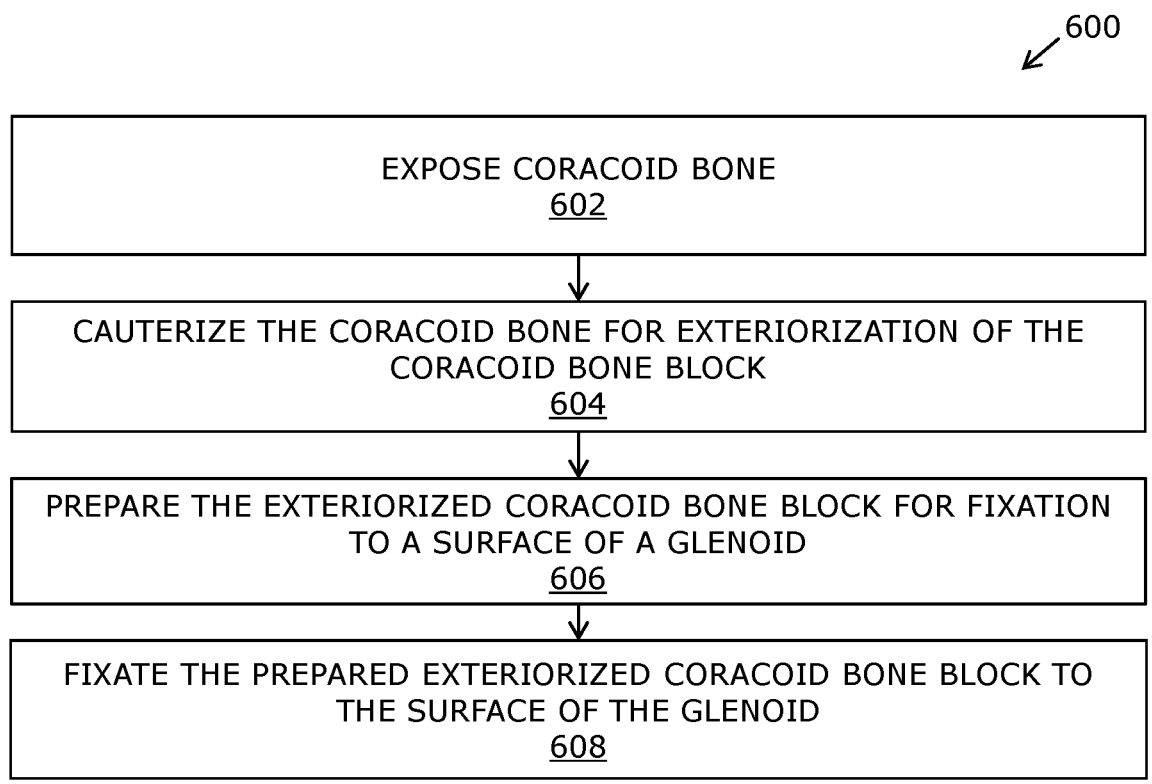
FIG. 6 is a schematic illustration of a flowchart illustrating steps of a method for using a coracoid guiding system, in accordance with an embodiment of the present disclosure.

Referring to FIG. 6, there is shown a flowchart illustrating steps of a method 600 for using a coracoid guiding system, in accordance with an embodiment of the present disclosure. At step 602, coracoid bone is exposed. At step 604, the coracoid bone cauterized for exteriorization of the coracoid bone block. At step 606, the exteriorized coracoid bone block is prepared for fixation to a surface of a glenoid. At step 608, the prepared exteriorized coracoid bone block is fixated to the surface of the glenoid.

The steps 602, 604, 606, and 608 are only illustrative and other alternatives can also be provided where one or more steps are added, one or more steps are removed, or one or more steps are provided in a different sequence without departing from the scope of the claims herein.

Figure 7:
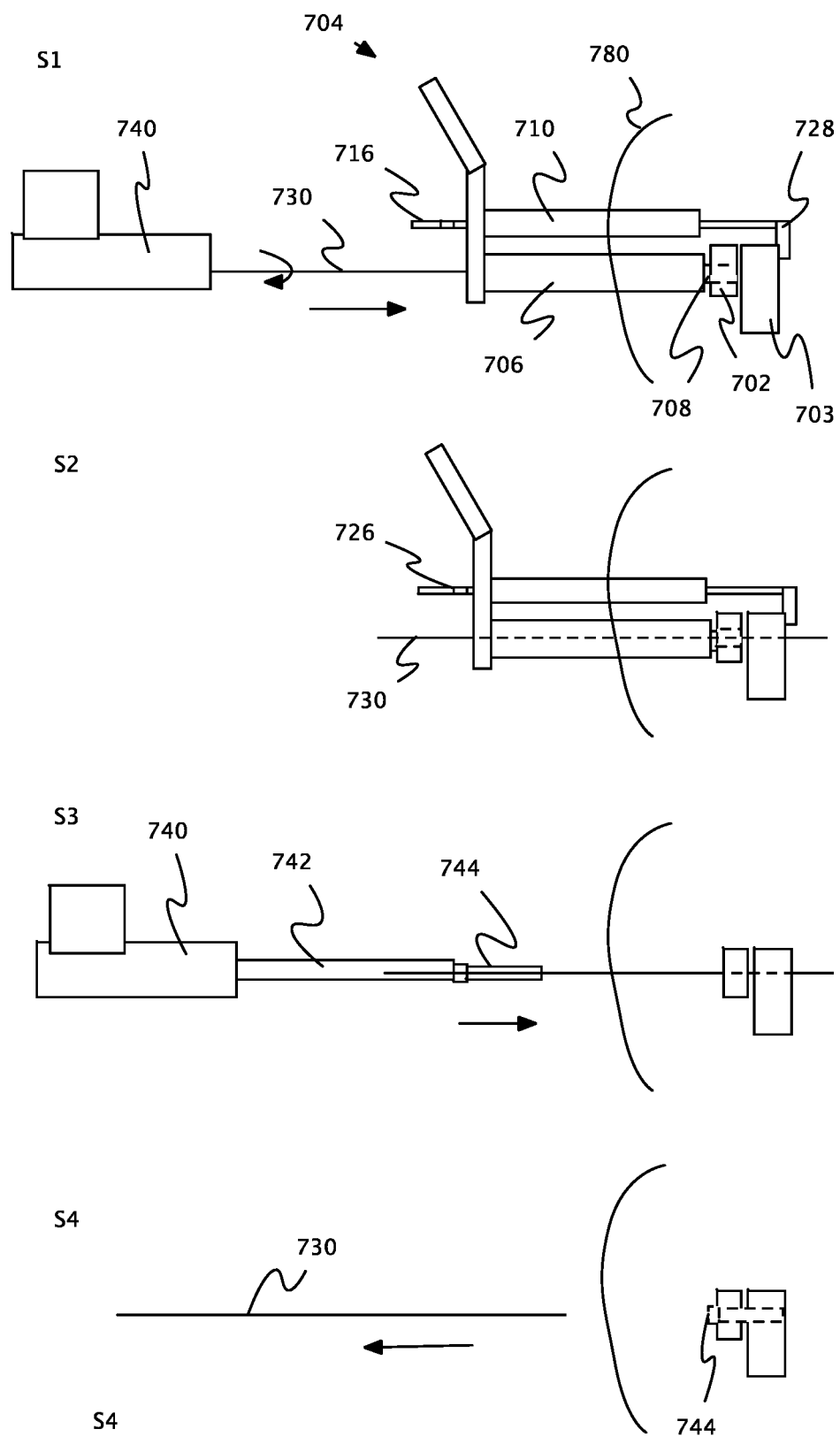
FIG. 7 is a schematic illustration of steps according to an embodiment of the present disclosure.

FIG. 7. is an example illustration of steps using the coracoid guiding system. In step S1 a coracoid passer 704 is inserted inside of a shoulder 780 of a patient. Internal barrel pins 708 (and are inside of external barrels 706) are arranged in drilled holes of an exteriorized coracoid bone block 702. A hook gauge 716 is used to align the exteriorized coracoid bone block with a glenoid 703. Scale points 726 (marking) of the hook gauge 716 can be used to determine relevant measurements. The hook gauge 716 is configured to move back and forth inside of hollow guiding tube 710. The hook gauge 716 has a curved section which is between proximal and distal end of the hook gauge 716 and, when in use, is inside of the hollow guiding tube 710. This way a sufficient friction between the hook gauge 716 and the hollow guiding tube 710 can be obtained to keep bone attached to the coracoid passer during operation. A drill 740 is used to drill a guide pin 730 thru glenoid. The guide pins 730 are inserted thru the opening of the internal barrel pins 708. This way the pins are precisely positioned in respect to drilled holes of the exteriorised coracoid bone block 702.

In step S2 of the FIG. 7 is illustrated a situation in which the guide pins 730 are drilled in.

In step S3 the drill 740 is used to screw a hollow screw 744. The hollow screw is dimensioned to fit around the guide pin 740. The drill 740 has holder 742 to attach screw to the drill.

Step S4 illustrates situation in which the hollow screw 744 is in its final position inside of the shoulder 780 of the patient. The hollow screw(s) 744 thus hold the exteriorized coracoid bone block together with glenoid 703. The guiding pints 730 are removed.

Figure 8:
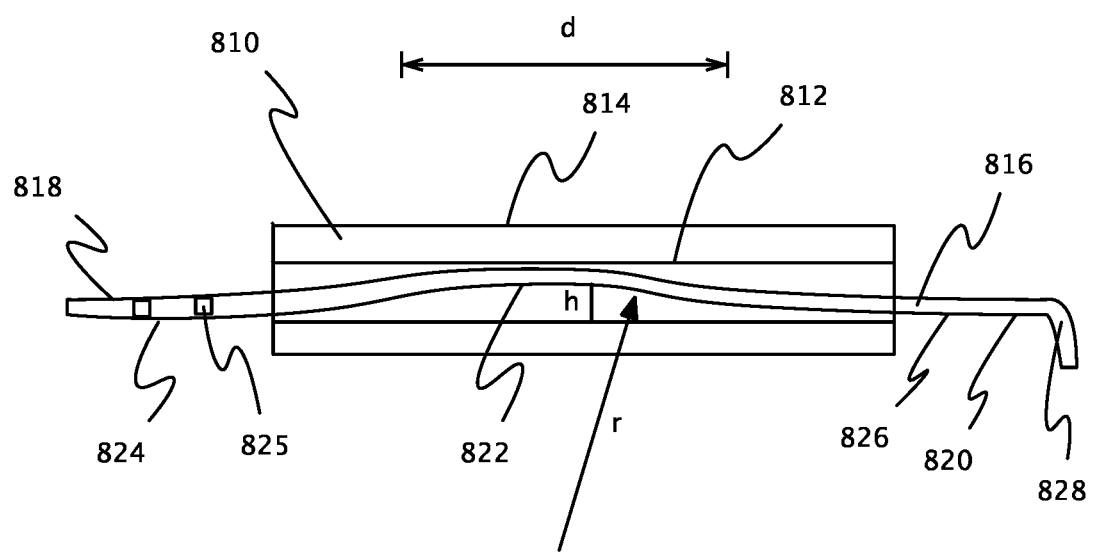
FIG. 8 is a schematic illustration of a detail of a hook gauge according to an embodiment of the present disclosure.

FIG. 8 is a detail of a hook gauge 816 arranged inside of a hollow guiding tube 810. The hollow guiding tube 810 comprising an inner surface 812 and an outer surface 814, the hook gauge 816 configured to be retractably arranged inside the hollow guiding tube 810, the hook gauge having a proximal end 818, a distal end 820, a curved section 822 between the proximal end and the distal end, a first straight section 824 extending from the proximal end to the curved section, a second straight section 826 extending from the curved section to the distal end, wherein the distal end of the hook gauge is shaped as a hook 828. The hook gauge 816 further comprises a scale points 825 i.e. measurement markings. Length of the curved section is d. Curvature radius of the curved section is r. There is gap h between the gauge and inner surface of the hollow guiding tube.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

What is claimed is:

1. A coracoid guiding system, the coracoid guiding system comprising
    a coracoid grasper for holding an exteriorized coracoid bone block,
    a coracoid passer configured to prepare the exteriorized coracoid bone block for fixation to a surface of a glenoid, the coracoid passer having
        a pair of external barrels,
        a pair of internal barrels pins,
        a hollow guiding tube comprising an inner surface and an outer surface, and
        a hook gauge configured to be retractably arranged inside the hollow guiding tube, the hook gauge having a proximal end, a distal end, a curved section between the proximal end and the distal end, a first straight section extending from the proximal end to the curved section, a second straight section extending from the curved section to the distal end, wherein the distal end of the hook gauge is shaped as a hook.

2. The coracoid guiding system according to claim 1, wherein the curved section of the hook gauge, and at least a part of the second straight section and/or the first straight section is arranged inside the hollow guiding tube, when in use.

3. The coracoid guiding system according to claim 1, wherein the diameter of the guiding tube is same as the diameter of the hook gauge.

4. The coracoid guiding system according to claim 1, wherein the curved section creates a frictional force between the inner surface (112) of the hollow guiding tube and at least a part of the hook gauge inside of the hollow guiding tube.

5. The coracoid guiding system according to claim 1, wherein the hook gauge comprises scale points to measure cross section of at least one of: the glenoid and the coracoid.

6. The coracoid guiding system according to claim 1, wherein the hook gauge is operable to hold the exteriorized coracoid bone block and the glenoid together, wherein the hook is in proximity with the glenoid and the second part traverses along the combined lengths of the glenoid and the exteriorized coracoid bone block.

7. The coracoid guiding system according to claim 1, wherein the coracoid bone block has a length of 20-25 mm, width of 10-14 and a thickness of 10-14 mm.

8. The coracoid guiding system according to claim 1, wherein the system further comprises a pair of guide pins to guide hollow screws for fastening the exteriorised coracoid bone block to the surface of the glenoid.

9. The coracoid guiding system according to claim 8, further comprising a screw extractor for withdrawing the hollow screws from the glenoid-coracoid bone block.

10. The coracoid guiding system according to claim 8, wherein length of the hollow screws is lesser that the combined lengths of the glenoid and the exteriorised coracoid bone block.

11. The coracoid guiding system according to claim 1, wherein preparing the exteriorised coracoid bone block comprises
    shaping of the exteriorised coracoid bone block,
    positioning drill holes in the exteriorised coracoid bone block, wherein the drill holes are longitudinally and transversely positioned, and
    placing the exteriorised coracoid bone block parallel to a surface of the glenoid, wherein the coracoid bone block is placed at a distance of 1-2 mm from the surface of the glenoid.

12. A kit comprising
a coracoid guiding system of claim 1,
a screw extractor and
guide pins.

13. The kit according to claim 12, further comprising screws for fastening the exteriorised coracoid bone block to the surface of the glenoid.

14. A coracoid passer configured to prepare an exteriorized coracoid bone block for fixation to a surface of a glenoid, the coracoid passer having
a pair of external barrels,
a pair of internal barrels,
a hollow guiding tube comprising an inner surface and an outer surface, and
a hook gauge configured to be retractably arranged inside the hollow guiding tube, the hook gauge having a proximal end, a distal end, a curved section between the proximal end and the distal end, a first straight section extending from the proximal end to the curved section, a second straight section extending from the curved section to the distal end, wherein the distal end of the hook gauge is shaped as a hook.

15. The coracoid passer according to claim 14, further comprising hollow screws for fastening the exteriorised coracoid bone block to the surface of the glenoid.

16. The coronoid passer according to claim 14, wherein the curved section has a radius r of curvature between 200 to 13000 mm.

17. A method for using a coracoid guiding system, the method comprising
exposing coracoid bone,
cauterization of the coracoid bone for exteriorization of the coracoid bone block,
preparing the exteriorized coracoid bone block for fixation to a surface of a glenoid, and
fixating the prepared exteriorized coracoid bone block to the surface of the glenoid.

18. The method according to the claim 17, wherein preparing the exteriorized coracoid bone block comprises
shaping of the exteriorized coracoid bone block,
positioning drill holes in the exteriorized coracoid bone block, wherein the drill holes are longitudinally and transversely positioned, and
placing the exteriorized coracoid bone block parallel to a surface of the glenoid, wherein the exteriorized coracoid bone block is placed at a distance of 1-2 mm from the surface of the glenoid.

19. The method according to claim 17, wherein the exteriorized coracoid bone block being placed parallel to the surface of the glenoid uses a frictional force between the inner surface of the hollow guiding tube an d at least a part of the hook gauge inside of the hollow guiding tube.

* * * * *